United States Patent
Chen et al.

(10) Patent No.: US 11,966,454 B2
(45) Date of Patent: Apr. 23, 2024

(54) SELF-CONTRASTIVE LEARNING FOR IMAGE PROCESSING

(71) Applicant: Shanghai United Imaging Intelligence Co., Ltd., Shanghai (CN)

(72) Inventors: Zhang Chen, Brookline, MA (US);
Xiao Chen, Lexington, MA (US);
Yikang Liu, Cambridge, MA (US);
Terrence Chen, Lexington, MA (US);
Shanhui Sun, Lexington, MA (US)

(73) Assignee: Shanghai United Imaging Intelligence Co., Ltd., Shanghai (CN)

( * ) Notice: Subject to any disclaimer, the term of this patent is extended or adjusted under 35 U.S.C. 154(b) by 427 days.

(21) Appl. No.: 17/513,493

(22) Filed: Oct. 28, 2021

(65) Prior Publication Data
US 2023/0138380 A1 May 4, 2023

(51) Int. Cl.
*G06K 9/00* (2022.01)
*G01R 33/56* (2006.01)
(Continued)

(52) U.S. Cl.
CPC ..... *G06F 18/2148* (2023.01); *G01R 33/5608* (2013.01); *G06N 3/08* (2013.01); *G06T 3/40* (2013.01); *G06T 5/70* (2024.01); *G06T 7/0014* (2013.01); *G06T 11/008* (2013.01); *G06V 10/95* (2022.01); *G16H 30/20* (2018.01); *G06T 2207/10088* (2013.01); *G06T 2207/20081* (2013.01); *G06T 2207/20084* (2013.01); *G06T 2207/30004* (2013.01)

(58) Field of Classification Search
CPC .... G06F 18/2148; G16H 30/20; G06V 10/95; G06T 5/70; G06T 3/40; G06T 7/0014; G06T 11/008; G06T 2207/10088; G06T 2207/20081; G06T 2207/20084; G06T 2207/30004; G01R 33/568; G06N 3/08
USPC ......................................... 382/132
See application file for complete search history.

(56) References Cited

U.S. PATENT DOCUMENTS

2017/0100078 A1\* 4/2017 Han .................... A61B 5/7278
2018/0018757 A1\* 1/2018 Suzuki ................. G06N 3/045
(Continued)

OTHER PUBLICATIONS

Kim et al., Adversarial Self-Supervised Contrastive Learning, Jun. 13, 2020.

Primary Examiner — Gabriel I Garcia
(74) Attorney, Agent, or Firm — Zhong Law LLC (57) ABSTRACT

A neural network system implements a model for generating an output image based on a received input image. The model is learned through a training process during which parameters associated with the model are adjusted so as to maximize a difference between a first image predicted using first parameter values of the model and a second image predicted using second parameter values of the model, and to minimize a difference between the second image and a ground truth image. During a first iteration of the training process the first image is predicted and during a second iteration the second image is predicted. The first parameter values are obtained during the first iteration by minimizing a difference between the first image and the ground truth image, and the second parameter values are obtained during the second iteration by maximizing the difference between the first image and the second image.

19 Claims, 6 Drawing Sheets

(51) Int. Cl.
   *G06F 18/214*   (2023.01)
   *G06N 3/08*     (2023.01)
   *G06T 3/40*     (2006.01)
   *G06T 5/70*     (2024.01)
   *G06T 7/00*     (2017.01)
   *G06T 11/00*    (2006.01)
   *G06V 10/94*    (2022.01)
   *G16H 30/20*    (2018.01)

(56) References Cited

U.S. PATENT DOCUMENTS

| | | | |
|---|---|---|---|
| 2019/0156502 A1* | 5/2019 | Lee | G06T 7/11 |
| 2022/0164601 A1* | 5/2022 | Lo | H04N 1/6086 |
| 2022/0342316 A1* | 10/2022 | Kooiman | G03F 7/70625 |
| 2023/0074706 A1* | 3/2023 | Xiao | G06F 18/213 |

\* cited by examiner

SELF-CONTRASTIVE LEARNING FOR IMAGE PROCESSING

BACKGROUND

Machine learning, especially deep learning, has been widely used in image processing tasks, such as image reconstruction, image de-noising, image super resolution, motion estimation, etc. Conventional deep learning-based image processing techniques often rely on annotated or high quality images as the ground truth for training an image processing model. However, the predictions (e.g., output images) from the trained model may still be of suboptimal quality when compared to the ground truth images. For example, magnetic resonance (MR) images reconstructed based on under-sampled k-space data from the trained model may be blurry compared to the fully sampled ground truth images. Similar problems (e.g., images being too noisy) also exist with the other noted image processing tasks when using only positive examples (e.g., ground truth images) for training the models. Accordingly, it may be desirable to utilize additional information, in combination with the ground truth images, to train the model for an image processing task.

SUMMARY

Described herein are neural network-based systems, methods and instrumentalities associated with medical image processing. In examples, the systems, methods, and instrumentalities may be implemented using processors and/or storage mediums including executable computer programs for utilizing machine learning technologies to implement a model for generating an output image based on an input image. An image processing neural network system (e.g., using one or more artificial neural networks which may include a convolutional neural network) may be trained to receive an input image of an anatomical structure (e.g., a myocardium, a cortex, a cartilage, etc.), the input image produced by a medical imaging modality, and generate an output image based on the input image. The image processing neural network system may be configured to implement a model for generating the output image based on the input image. The model may be learned through a training process during which parameters associated with the model are adjusted so as to maximize a difference between a first image (e.g., an output image) predicted using first parameter values of the model and a second image predicted using second parameter values of the model, and to minimize a difference between the second image and a ground truth image.

The image processing neural network system may be trained according to a process comprising a first iteration and a second iteration. The first image may be predicted during the first iteration and the second image may be predicted during the second iteration. The first parameter values of the model may be obtained during the first iteration by minimizing a difference between the first image and the ground truth image. The second parameter values of the model may be obtained during the second iteration by maximizing the difference between the first image and the second image. The first iteration of the training process may be conducted under a different training setting than the second iteration of the training process.

In embodiments, the image processing neural network system may determine the difference between the first image and the second image, or the difference between the second image and the ground truth image based on an L1 norm, an L2 norm, or a hinge loss. In embodiments, a triplet loss function may be used during the training process to maximize the difference between the first image and the second image, and to minimize the difference between the second image and the ground truth image.

In embodiments, the medical imaging modality may be a magnetic resonance imaging (MRI) scanner and the input image may be an MRI image. In embodiments, the input image may be an under-sampled MRI image of the anatomical structure (e.g., a myocardium, a cortex, a cartilage, etc.) and the output image may be a fully-sampled MRI image of the anatomical structure.

In embodiments, the output image may be a higher resolution version of the input image or the output image may be a de-noised version of the input image.

BRIEF DESCRIPTION OF THE DRAWINGS

The disclosure will be understood more fully from the detailed description given below and from the accompanying drawings of various embodiments of the disclosure. The drawings, however, should not be taken to limit the disclosure to the specific embodiments, but are for explanation and understanding only.

DETAILED DESCRIPTION

Figure 1:
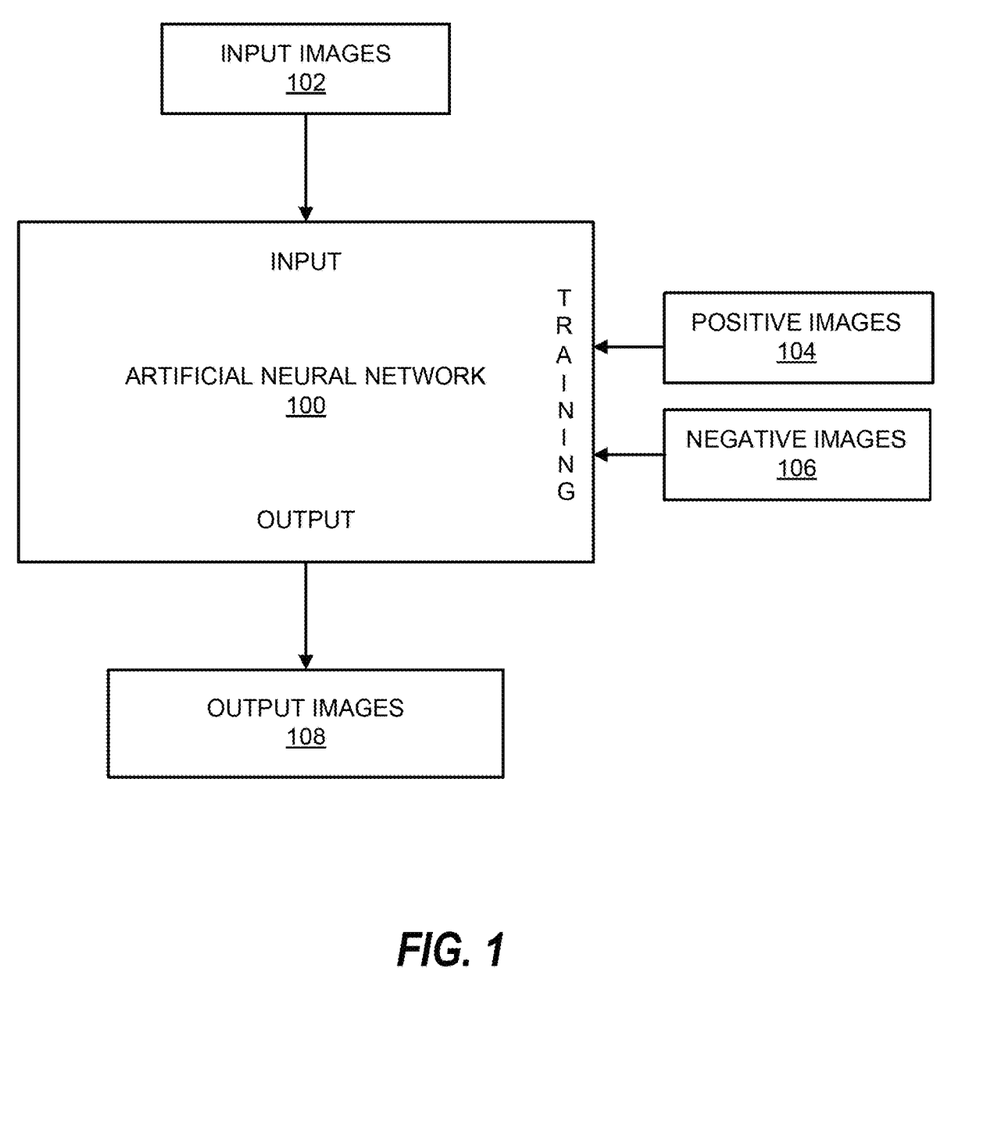
FIG. 1 shows a simplified block diagram of an example image processing neural network system as described herein.

FIG. 1 shows a simplified block diagram of an example image processing neural network system as described herein. The neural network system may comprise an artificial neural network (ANN) 100 such as a deep convolutional neural network (DCNN) that may include multiple layers, such as an input layer for receiving data inputs (e.g., input images 102), an output layer for generating outputs (e.g., output images 108), and one or more hidden layers. The hidden layers may include one or more convolutional layers, one or more pooling layers, and/or one or more fully connected layers. Each of the convolutional layers may include a plurality of convolution kernels or filters configured to extract specific features from the input images 102. The convolution operation may be followed by batch normalization and/or non-linear activation, and the features extracted by the convolutional layers (e.g., in the form of one or more feature maps) may be down-sampled through the pooling layers and/or the fully connected layers (e.g., using a 2×2 window and a stride of 2) to reduce the redundancy and/or dimension of the features (e.g., by a factor of 2).

In embodiments, the input images 102 may comprise an image of an anatomical structure (e.g., a myocardium, a cortex, a cartilage, etc.) produced by a medical imaging modality. In embodiments, such a medical imaging modality may comprise a magnetic resonance imaging (MRI) scanner so that input images 102 may comprise an MRI image. In embodiments, the input images 102 may comprise an under-sampled MRI image of the anatomical structure and the output images 108 may comprise a fully-sampled or otherwise adapted (e.g., higher resolution, less noise, etc.) MRI image of the anatomical structure. In embodiments, the input images 102 may be derived based on under-sampled MRI data (e.g., k-space data) by applying a Fourier transform (e.g., a fast Fourier transform or FFT) to the under-sampled MRI data.

The artificial neural network 100 may be configured to implement an image processing model for generating the output images 108 based on the input images 102, and the model may be learned through a contrastive training process utilizing one or more positive images 104 and one or more negative images 106. The positive images 104 may refer to ground truth images obtained for training the image processing model while the negative images 106 may refer to images generated using preliminary (e.g., coarse) parameters of the image processing model. The training may be conducted in a contrastive manner, for example, by maximizing a difference between an image predicted by the artificial neural network 100 (e.g., an output image 108) and a negative image 106 and to minimize a difference between the predicted image and a positive image 104. For example, the training of the neural network 100 (e.g., the image processing model implemented by the neural network 100) may comprise multiple rounds or iterations. In a first round or iteration, the neural network 100 may be trained to predict an output image (e.g., an adapted version of the input image 102) that resembles a ground truth for the adapted image. The neural network 100 may do so, for example, by adjusting its parameters to minimize the difference between the predicted image and the ground truth image. In the second round or iteration of the training, the neural network 100 may be further trained using images predicted during the first round or iteration of the training as negative images 106 and ground truth images as positive images 104, and the neural network 100 may further adjust its parameters by minimize the differences between images predicted by the neural network and the positive images 104 and by maximizing the differences between the images predicted by the neural network and the negative images 106.

In embodiments, the neural network may be configured to implement (e.g., learn) a first model during the first round or iteration of the training and implement (e.g., learn) a second model (e.g., different than the first model) during the second round or iteration of the training. The first round or iteration of the training may be conducted based on a first loss function such as a L1 or L2 loss function (e.g., to minimize the difference between a predicted image and a ground truth image) and the second round or iteration of the training may be conducted based on a second loss function such as a triplet loss function (e.g., to minimize the difference between a predicted image and a positive or ground truth image and to maximize the difference between the predicted image and a negative image).

In embodiments, the neural network 100 may be configured to implement (e.g., learn) a same model through the first round or iteration of the training and the second round or iteration of the training. The neural network 100 may adjust the parameters of the model during both the first and the second rounds or iterations of the training based on a triple loss function. As described herein, the neural network 100 may use outputs from a previous iteration of the training as negative examples during a subsequent iteration of the training (e.g., to steer the neural network from the negative examples). As such, at the beginning of the training (e.g., when there is no previous iteration), the neural network 100 may use a randomly generated image (or a blank/empty image) as the negative example.

The images predicted by the neural network 100 during a previous round or iteration of the training may be used as negative examples to guide the training because the quality of such initially generated images may not be satisfactory (e.g., the images may be blurry compared to the ground truth). By forcing the neural network 100 to pull away from such negative examples and move towards positive examples during a subsequent round or iteration of the training, the parameters of the neural network 100 may be further optimized. Such a training/learning process may be referred to as a self-contrastive training/learning process since the outputs generated by the neural network 100 from an earlier around or iteration of the training (e.g., using the same model) may be used as the negative images 106 during subsequent round(s) or iteration(s) of the training. Examples of such a self-contrast training/learning process will be further described below with reference to FIG. 3 and FIG. 4.

The neural network 100, as shown in FIG. 1, is an illustrative network that generates an output image 108 based on an input image 102. Implementations of the disclosure are not limited to a specific type of image processing tasks. For example, the input image 102 may be any image that may benefit from some form of image processing, such as image reconstruction, image de-noising, image super resolution, motion estimation, etc.

Figure 2:
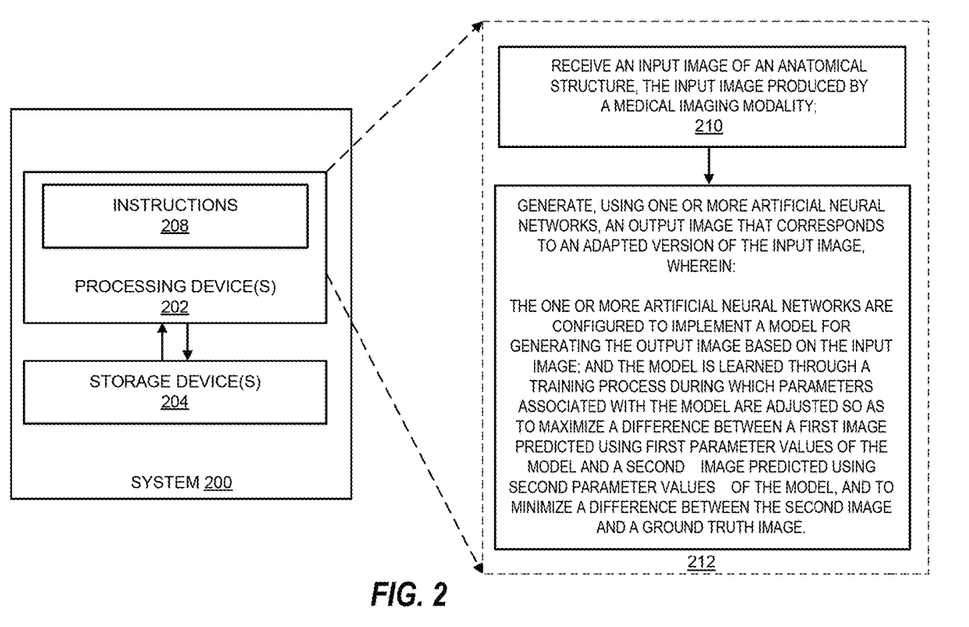
FIG. 2 shows a simplified block diagram of an example system that may be used to perform the image processing tasks described herein.

FIG. 2 shows a simplified block diagram of an example system (e.g., apparatus) 200 that may be used to perform the image processing tasks described herein. System 200 may be a standalone computer system or a networked computing resource implemented in a computing cloud, and may include processing device(s) 202 and storage device(s) 204, where the storage device 204 may be communicatively coupled to processing device 202. Processing device(s) 202 may include one or more processors such as a central processing unit (CPU), a graphic processing unit (GPU), or an accelerator circuit. Storage device(s) 204 may be a memory device, a hard disc, or a cloud storage device connected to processing device 202 through a network interface card (not shown in FIG. 2). Processing device(s) 202 may be programmed to implement a pre-learned image processing model described herein via instructions 208 (e.g., the instructions 208 may realize an artificial neural network for implementing the pre-learned model).

The processing device(s) 202 may execute instructions 208 and perform the following operations: at 210, receive an input image (e.g., input image 102 of FIG. 1) that may comprise an image of an anatomical structure produced by a medical imaging modality, such as an MRI scanner so that input image may comprise an MRI image; at 212, generate, using the artificial neural network (e.g., which may be trained to implement the image processing model), an output image (e.g., output image 108 of FIG. 1) that corresponds to an adapted version (e.g., reconstructed, higher resolution, less noise, etc.) of the input image. As noted above, the artificial neural network trained using the techniques described herein may be used for various image processing tasks with respect to the input image including, for example, image reconstruction, super resolution, denoising, etc.

As described herein, the artificial neural network may be trained to learn the image processing model through contrastive learning (e.g., self-contrastive learning, as described in association with FIG. 1) for generating the output image based on the input image. For example, the model may be learned through a training process during which parameters associated with the model are adjusted so as to maximize a difference between a first image (e.g., a negative image) predicted using first or preliminary parameter values of the model and a second image predicted using second or refined parameter values of the model, and minimizing a difference between the second image and a ground truth image (e.g., a positive image). As noted above, in embodiments, the training process may comprise first and second iterations during which the first and second images are predicted. The first parameter values may be obtained during the first iteration (e.g., guided by only ground truth images) by minimizing a difference between the first image and the ground truth image. The second parameter values may be obtained during the second iteration (e.g., guided by negative and/or positive images) by maximizing the difference between the first image and the second image and/or minimizing the difference between the second image and the ground truth image.

Figure 3:
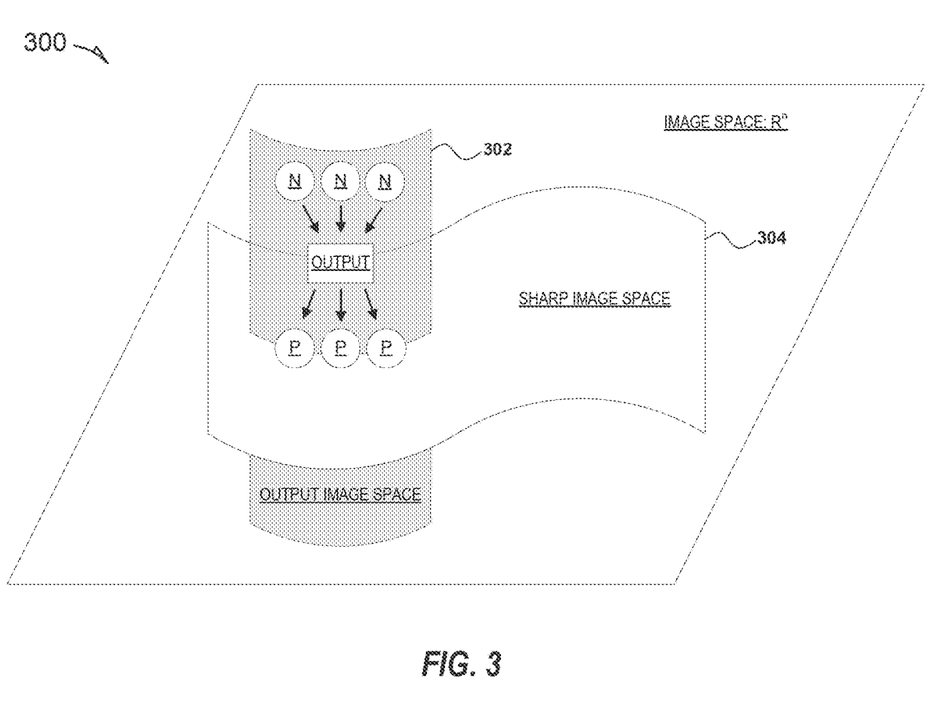
FIG. 3 shows a simplified diagram illustrating the effect of image processing by a neural network system as described herein.

FIG. 3 shows a simplified diagram illustrating the effect of image processing 300 by a neural network system as described herein. The shaded area 302 in FIG. 3 may represent the portion of the image space $R''$ associated with an output (e.g., output image 108 of FIG. 1) of the neural network system. The non-shaded area 304 in FIG. 3 may represent the portion of the image space $R''$ associated with a desired output (e.g., positive image 104 of FIG. 1). As shown, the self-contrastive training/learning may have the effect of forcing the neural network to refine its parameters so that the output produced by the neural network is pushed away from the negative results (e.g., the section of space 302 denoted "N" that lies outside of the desired space 304) and towards the positive results (e.g., the section of space 302 denoted "P" that lies inside the desired space 304.

In embodiments, the output images, positive images, and negative images may be represented in the image space $R''$ by respective feature maps or features vectors associated with the various images. In embodiments, the distances, in the image space $R''$, between the representation of the output images and the representations of the positive images P and between the representation of the output and the representation of the negative images N may be measured according to a specified loss function. In embodiments, the loss function may be based on, for example, an L1 norm, an L2 norm, or a hinge loss. In embodiments, such as that of FIG. 3, the loss function may comprise a triplet loss function designed to maximize the distance in the image space $R''$ between the output of the neural network and the negative images N, and to minimize the distance in the image space $R''$ between the output of the neural network and the representations of the positive images P.

Parameters associated with the neural network system may then be updated based on the maximizing and minimizing so that the representation of the output is pushed away from a location within an output image space that contains the representations of the negative images N (which may be previously predicted output images that were suboptimal) and is pulled closer to a location within the output image space that contains the representations of the positive images P (e.g., location where the output image space 302 intersects the sharp image space 304).

Figure 4:
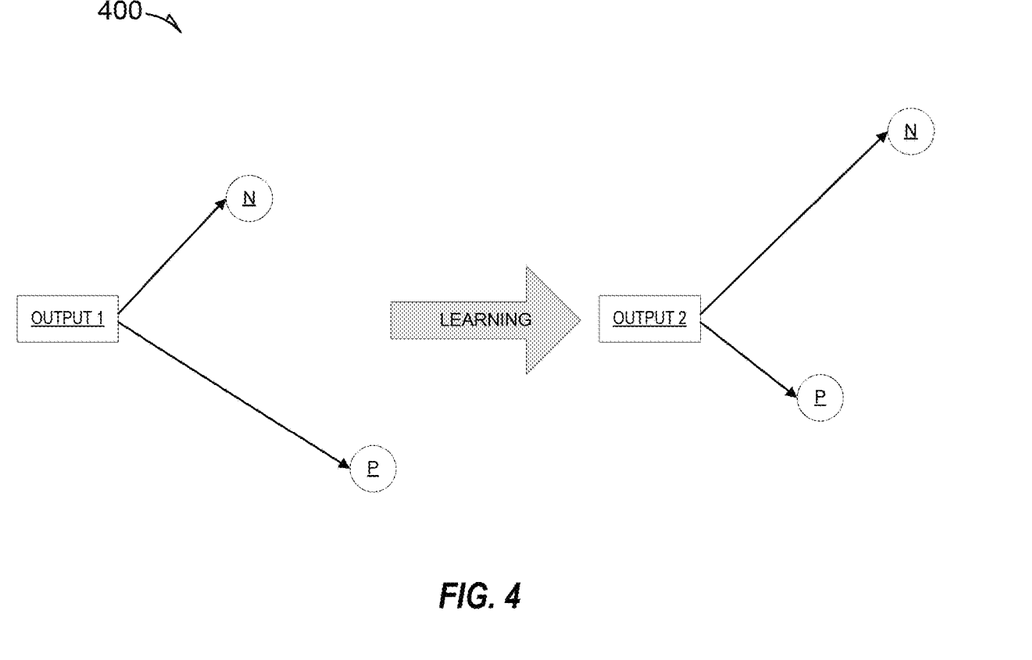
FIG. 4 shows a simplified diagram illustrating the use of a triplet loss function to learn a neural network model as described herein.

FIG. 4 shows a simplified diagram illustrating an example use 400 of a triplet loss function to learn an image processing model (e.g., learn parameters of an image processing neural network) as described herein.

Output 1 may be a representation of a first predicted image (e.g., an output image 108 of FIG. 1) in an image space (e.g., $R''$ of FIG. 3) and Output 2 may be a representation of a second predicted image (e.g., another output image 108 of FIG. 1) in the image space. Output 1 may be generated, for example, during a first iteration of training and Output 2 may be generated, for example, during a second iteration of training. During the training/learning process of the neural network described herein (e.g., with respect to neural network 100 of FIG. 1 and system 200 of FIG. 2), the parameters (e.g., weights) of the neural network may be adjusted based on a triplet loss function such that a later output (e.g., Output 2) may be closer to P (e.g., a positive image) and farther away from N (e.g., a negative images) compared to an earlier output (e.g., Output 1).

The triplet loss function may be expressed, for example, as:

$$L = \max(d(\text{output1}, P) - d(\text{output1}, N) - \text{margin}, 0)$$

wherein the margin may be a configurable parameter that forces the distances (d) between output1 and P and output 1 and N to be larger than the margin. The triplet loss function may be minimized so that the distance d(output1,P) is pushed towards 0 and the distance d(output 1, N) is pushed towards d(output 1, P)+margin. Accordingly, after the model is trained the output 2 corresponding to a subsequent predicted output image may be closer to P than previous output 1 and further away from N than previous output 1.

Figure 5:
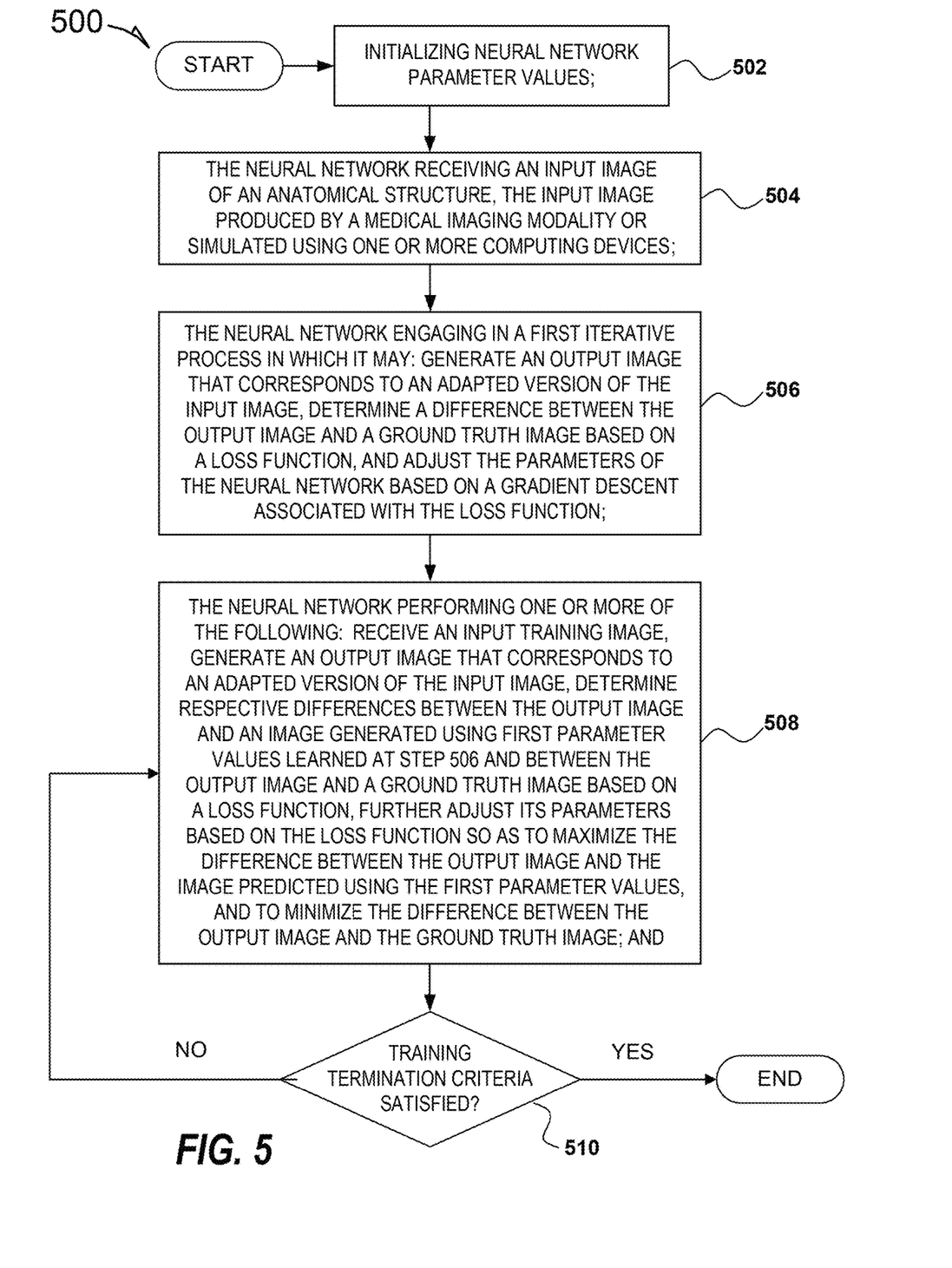
FIG. 5 shows a flow diagram of an example method for training a neural network for image processing as described herein.

FIG. 5 shows a flow diagram of an example method 500 for training a neural network for image processing as described herein. Method 500 may be performed by processing devices that may comprise hardware (e.g., circuitry, dedicated logic), computer readable instructions (e.g., run on a general purpose computer system or a dedicated machine), or a combination of both.

The method 500 may start and, at 502, operating parameters of the neural network may be initialized (e.g., weights associated with one or more layers of the neural network). For example, the parameters may be initialized based on samples from one or more probability distributions or parameter values of another neural network with a similar architecture.

At 504, the neural network may receive an input image (e.g., a training image) of an anatomical structure. The input image may be produced by a medical imaging modality or may be simulated using one or more computing devices. As noted above, the medical imaging modality may comprise an MRI scanner so that the input image of an anatomical structure comprises an MRI image.

At 506, the neural network may engage in a first iterative process (e.g., a first round of training or a first stage of the training process) in which the neural network may generate an output image that corresponds to an adapted version (e.g., reconstructed, higher resolution, less blurry, etc.) of the input image, determine a difference between the output image and a ground truth image based on a loss function (e.g., an L1 loss function, an L2 loss function, a hinge loss function, etc.), and adjust the parameters of the neural network based on a gradient descent associated with the loss function. The neural network may repeat the above operations for a number (e.g., preconfigured number) of iterations or until full convergence, and this iterative process may constitute a first round or iteration of the training.

At 508, the neural network may perform one or more of the following. The neural network may receive an input training image (e.g., as described herein), generate an output image that corresponds to an adapted version (e.g., reconstructed, higher resolution, less blurry, etc.) of the input training image and determine respective differences between the output image and a negative image and between the output image and a positive image based on a loss function (e.g., a triplet loss function). The negative image may be generated based on the input training image and the first parameter values learned at 506 (e.g., by feeding the input training image to the model learned in the first round of training) while the positive image may be a ground truth image. The neural network may then adjust its parameters based on the loss function (e.g., a gradient descent of the loss function) so as to maximize the difference between the output image and the negative image and to minimize the difference between the output image and the positive image.

At 510, the neural network may determine whether one or more training termination criteria are satisfied. For example, the neural network may determine that the training termination criteria are satisfied if the neural network has completed a predetermined number of training iterations, or if the difference between the output image predicted by the network and the ground truth image is below a predetermined threshold. If the determination at 510 is that the training termination criteria are not satisfied, the system may return to 508. If the determination at 510 is that the training termination criteria are satisfied, the method 500 may end. The operations associated with 508 and 510 may constitute a second iteration of the training (e.g., a second round of training or a second stage of the training process).

The first and second rounds of training described herein may be conducted under the same settings (e.g., same epoches) or under different settings (e.g., different epochs). The first and second rounds of training described herein may be conducted based on a same model (e.g., parameters of the model may be adjusted between the first and second rounds) or based on different models (e.g., the negative images used to facilitate the second round of training may be generated using one or more models that are different than the model trained in the second round). If the negative images are generated using multiple models, those models may be trained under a same set of settings or under different sets of settings.

For simplicity of explanation, the operation of the method 500 is depicted and described herein with a specific order. It should be appreciated, however, that these operations may occur in various orders, concurrently, and/or with other operations not presented or described herein. Furthermore, it should be noted that not all operations that the neural network system is capable of performing are depicted and described herein, and not all illustrated operations of method 500 are required to be performed by the system.

Figure 6:
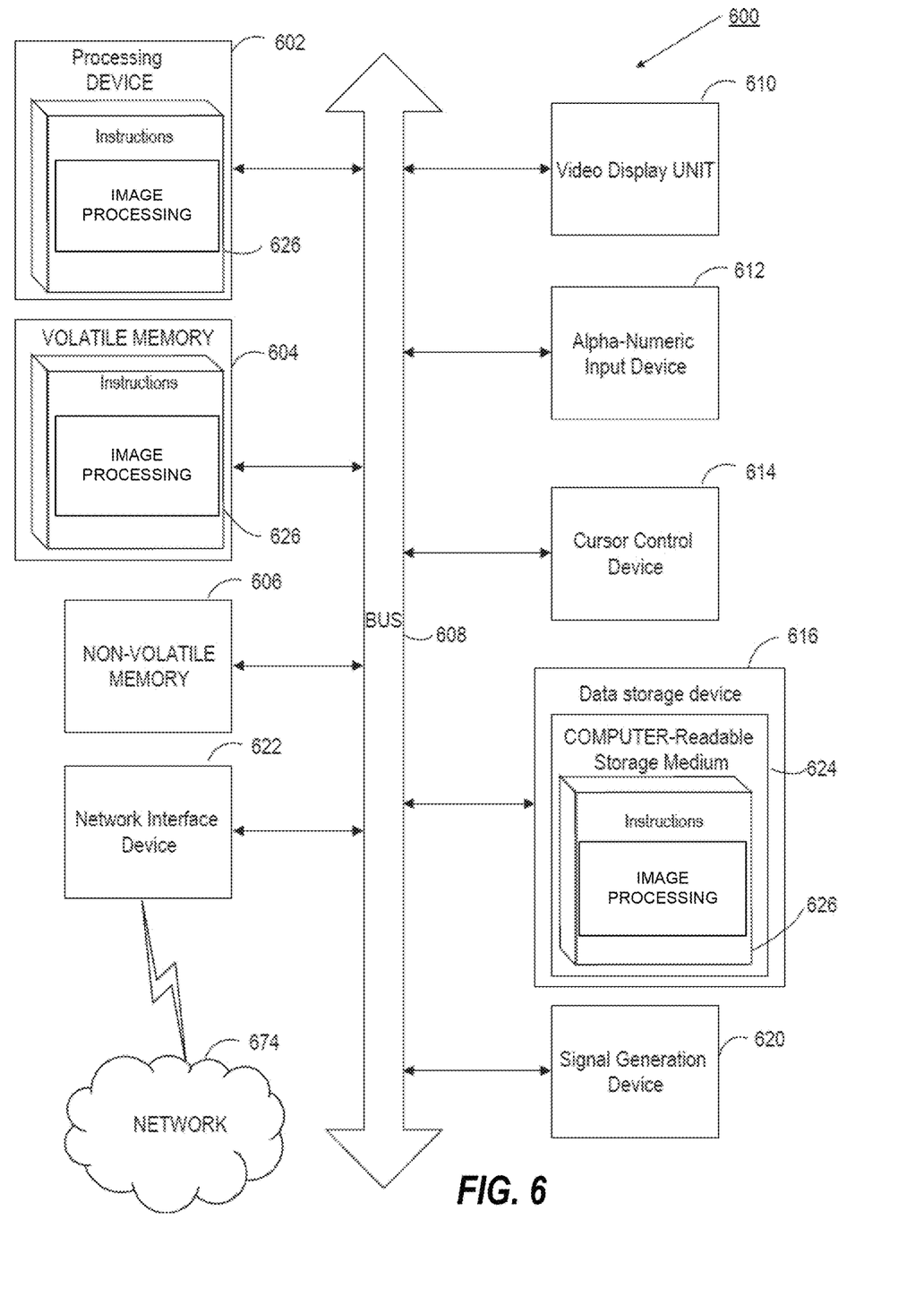
FIG. 6 shows a simplified block diagram illustrating an example neural network system for performing image processing as described herein.

FIG. 6 shows a simplified block diagram illustrating an example neural network system 600 for performing image processing as described herein. In embodiments, neural network system 600 may be connected (e.g., via a network, such as a Local Area Network (LAN), an intranet, an extranet, or the Internet) to other computer systems. Neural network system 600 may operate in the capacity of a server or a client computer in a client-server environment, or as a peer computer in a peer-to-peer or distributed network environment. Neural network system 600 may be provided by a personal computer (PC), a tablet PC, a set-top box (STB), a Personal Digital Assistant (PDA), a cellular telephone, a web appliance, a server, a network router, switch or bridge, or any device capable of executing a set of instructions (sequential or otherwise) that specify actions to be taken by that device. Further, the term "computer" shall include any collection of computers that individually or jointly execute a set (or multiple sets) of instructions to perform any one or more of the methods described herein.

Furthermore, the neural network system 600 may include a processing device 602 (e.g., processing device(s) 202 of FIG. 2), a volatile memory 604 (e.g., random access memory (RAM)), a non-volatile memory 606 (e.g., read-only memory (ROM) or electrically-erasable programmable ROM (EEPROM)), and a data storage device 616 (e.g., storage device(s) 204 of FIG. 2), which may communicate with each other via a bus 608. Processing device 602 may be provided by one or more processors such as a general purpose processor (such as, for example, a complex instruction set computing (CISC) microprocessor, a reduced instruction set computing (RISC) microprocessor, a very long instruction word (VLIW) microprocessor, a microprocessor implementing other types of instruction sets, or a microprocessor implementing a combination of types of instruction sets) or a specialized processor (such as, for example, an application specific integrated circuit (ASIC), a field programmable gate array (FPGA), a digital signal processor (DSP), or a network processor).

Neural network system 600 may further include a network interface device 622, a video display unit 610 (e.g., an LCD), an alphanumeric input device 612 (e.g., a keyboard), a cursor control device 614 (e.g., a mouse), a data storage device 616, and/or a signal generation device 620. Data storage device 616 may include a non-transitory computer-readable storage medium 624 on which may store instructions 626 encoding any one or more of the image processing methods or functions described herein. Instructions 626 may also reside, completely or partially, within volatile memory 604 and/or within processing device 602 during execution thereof by computer system 600, hence, volatile memory 604 and processing device 602 may also constitute machine-readable storage media.

While computer-readable storage medium 624 is shown in the illustrative examples as a single medium, the term "computer-readable storage medium" shall include a single medium or multiple media (e.g., a centralized or distributed database, and/or associated caches and servers) that store the one or more sets of executable instructions. The term "computer-readable storage medium" shall also include any tangible medium that is capable of storing or encoding a set of instructions for execution by a computer that cause the computer to perform any one or more of the methods described herein. The term "computer-readable storage medium" shall include, but not be limited to, solid-state memories, optical media, and magnetic media.

The methods, components, and features described herein may be implemented by discrete hardware components or may be integrated in the functionality of other hardware components such as ASICS, FPGAs, DSPs or similar devices. In addition, the methods, components, and features may be implemented by firmware modules or functional circuitry within hardware devices. Further, the methods, components, and features may be implemented in any combination of hardware devices and computer program components, or in computer programs.

The invention claimed is:

1. An apparatus comprising one or more processors and one or more storage devices, the one or more storage devices configured to store instructions that, when executed by the one or more processors, cause the one or more processors to:

receive an input image of an anatomical structure, the input image produced by a medical imaging modality; and generate, using one or more artificial neural networks, an output image based on the input image, wherein:
the one or more artificial neural networks are configured to implement a model for generating the output image based on the input image; and
the model is learned through a training process during which parameters associated with the model are adjusted so as to maximize a difference between a first image predicted using first parameter values of the model and a second image predicted using second parameter values of the model, and to minimize a difference between the second image and a ground truth image.

2. The apparatus of claim 1, wherein the training process comprises a first iteration and a second iteration, the first image is predicted during the first iteration, the second image is predicted during the second iteration, the first parameter values of the model are obtained during the first iteration by minimizing a difference between the first image and the ground truth image, and the second parameter values of the model are obtained during the second iteration by maximizing the difference between the first image and the second image.

3. The apparatus of claim 2, wherein the first iteration of the training process is conducted under a different training setting than the second iteration of the training process.

4. The apparatus of claim 1, wherein at least one of the difference between the first image and the second image, or the difference between the second image and the ground truth image is determined based on an L1 norm, an L2 norm, or a hinge loss.

5. The apparatus of claim 1, wherein a triplet loss function is used during the training process to maximize the difference between the first image and the second image, and to minimize the difference between the second image and the ground truth image.

6. The apparatus of claim 1, wherein the medical imaging modality comprises a magnetic resonance imaging (MRI) scanner, the input image comprises an under-sampled MRI image, and the output image comprises a reconstructed MRI image.

7. The apparatus of claim 6, wherein the reconstructed MRI image has the quality of a fully-sampled MRI image.

8. The apparatus of claim 1, wherein the output image comprises a higher resolution version of the input image.

9. The apparatus of claim 1, wherein the output image comprises a de-noised version of the input image.

10. The apparatus of claim 1, wherein the one or more artificial neural networks comprise a convolutional neural network.

11. A method for image processing implemented by a neural network system, the method comprising:
the neural network system receiving an input image of an anatomical structure, the input image produced by a medical imaging modality; and
the neural network system generating, using one or more artificial neural networks, an output image based on the input image, wherein:
the one or more artificial neural networks are configured to implement a model for generating the output image based on the input image; and
the model is learned through a training process during which parameters associated with the model are adjusted so as to maximize a difference between a first image predicted using first parameter values of the model and a second image predicted using second parameter values of the model, and to minimize a difference between the second image and a ground truth image.

12. The method of claim 11, wherein the training process comprises a first iteration and a second iteration, the first image is predicted during the first iteration, the second image is predicted during the second iteration, the first parameter values of the model are obtained during the first iteration by minimizing a difference between the first image and the ground truth image, and the second parameter values of the model are obtained during the second iteration by maximizing the difference between the first image and the second image.

13. The method of claim 12, wherein the first iteration of the training process is conducted under a different training setting than the second iteration of the training process.

14. The method of claim 11, wherein at least one of the difference between the first image and the second image, or the difference between the second image and the ground truth image is determined based on an L1 norm, an L2 norm, or a hinge loss.

15. The method of claim 11, wherein a triplet loss function is used during the training process to maximize the difference between the first image and the second image, and to minimize the difference between the second image and the ground truth image.

16. The method of claim 11, wherein the medical imaging modality comprises a magnetic resonance imaging (MRI) scanner, the input image comprises an under-sampled MRI image of the anatomical structure, and the output image comprises a reconstructed MRI image.

17. The method of claim 11, wherein the output image comprises a higher resolution version of the input image or a de-noised version of the input image.

18. A method of training a neural network for image processing, the method comprising:
initializing parameters of the neural network;
during a first round of training:
receiving a first training image;
predicting a first output image corresponding to an adapted version of the first training image; and
adjusting the parameters of the neural network so as to minimize a difference between the first output image and a first ground truth image; and
during a second round of training:
receiving a second training image;
predicting a second output image corresponding to an adapted version of the second training image; and
adjusting the parameters of the neural network so as to maximize a difference between the second output image and a negative image and minimize a difference between the second output image and a second ground truth image, wherein the negative image is obtained based on the second training image using the parameters of the neural network learned during the first round of training.

19. The method of claim 18, wherein each of the first training image and the second training image comprises an under-sampled magnetic resonance imaging (MRI) image, and wherein the each of the first output image and the second output image comprises a reconstructed MRI image.

* * * * *